United States Patent [19]

Cheng et al.

[11] 4,265,107
[45] May 5, 1981

[54] PORTABLE AIRBORNE DROPLET IMPACTOR SAMPLER AND METHOD

[75] Inventors: Lung Cheng, McMurray; Warren G. Cross, Library, both of Pa.

[73] Assignee: The United States of America as represented by the Secretary of the Interior, Washington, D.C.

[21] Appl. No.: 104,922

[22] Filed: Dec. 18, 1979

[51] Int. Cl.³ ............................................ G01N 15/02
[52] U.S. Cl. ................................... 73/28; 73/432 PS
[58] Field of Search ............... 73/28, 421 R, 421.5 R, 73/432 PS; 55/270

[56] References Cited

U.S. PATENT DOCUMENTS 3,653,253  4/1972  Olin .................................. 73/432 PS

OTHER PUBLICATIONS

K. R. May; "Measurement of Airborne Droplets by the Magnesium Oxide Method", *Journal of Scientific Instruments,* vol. 27, pp. 128–130, May 1950.

S. G. Gathman; "Airborne Droplet Sampler For Use in Fogs and Low-Level Stratus", *Journal of Applied Meteorology,* vol. 14, pp. 1293–1296, Oct. 1975.

L. Cheng; "Stain Method For Measurement of Drop Size", *Environmental Science and Technology,* ol. 11, No. 2, pp. 192–194, Feb. 1977.

L. Cheng; "Dynamic Spreading of Drops Impacting Onto a Solid Surface", *Ind. Eng. Chem., Process Des. Dev.,* vol. 16, No. 2, pp. 192–197, Apr. 1977.

*Primary Examiner*—Stephen A. Kreitman
*Attorney, Agent, or Firm*—Gersten Sadowsky; Donald A. Gardiner

[57] ABSTRACT

A droplet impact sampler based upon the stain technique for measuring airborne droplets comprises a magnesium oxide coated, graphite target located within a cylindrical sampler head below a pneumatically operated shutter. The shutter is opened for a predetermined time period to expose the target to the specimen droplets which stain the target upon contact. Droplet size is determined by measuring the stain diameters and compensating for a flattening effect of the droplet that occurs upon impact as a function of several parameters, such as contact angle, water density and surface tension. Rate of deposition is determined by correlating the number of stains counted on the target with the operating speed of the shutter.

16 Claims, 9 Drawing Figures

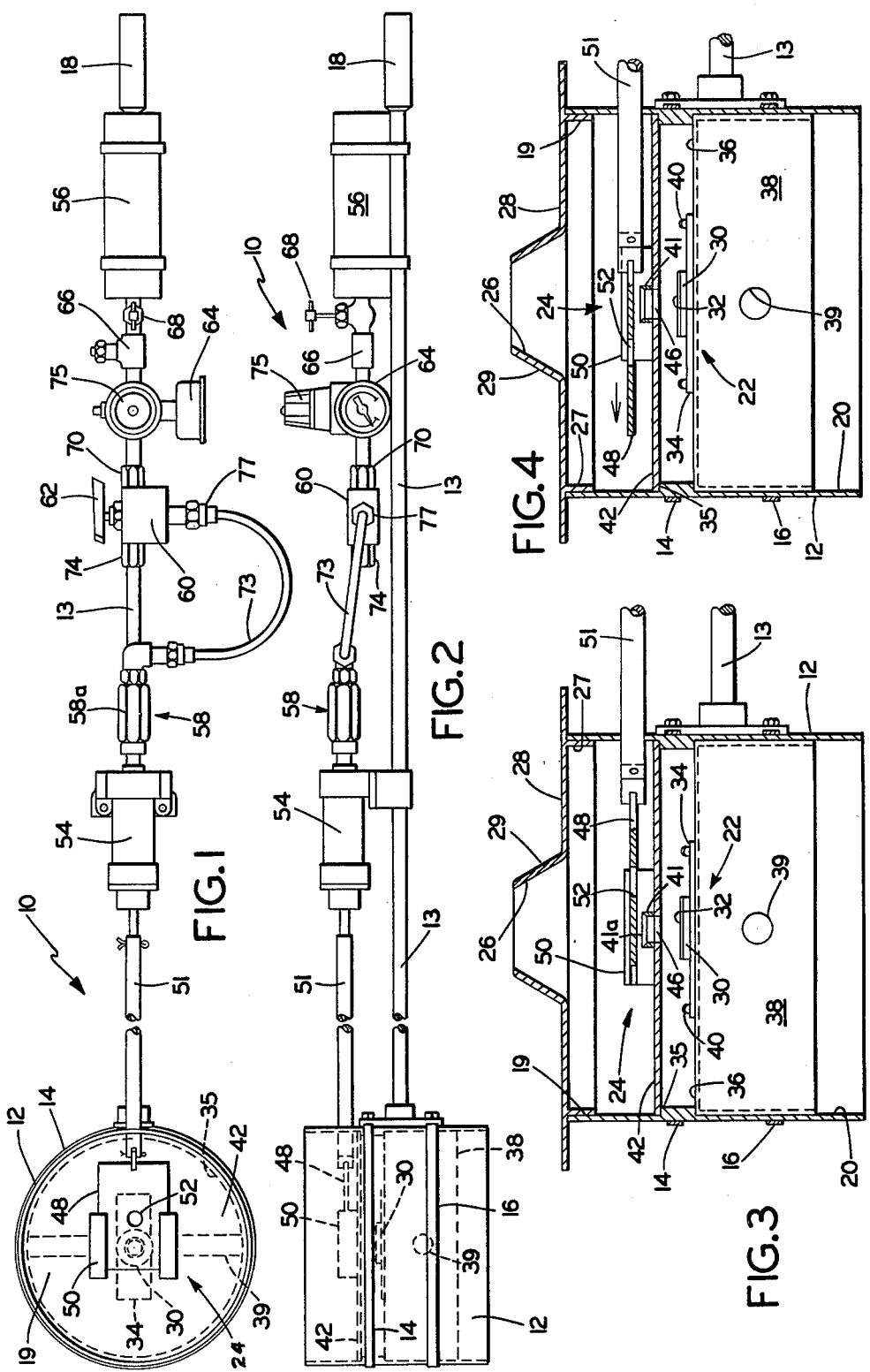

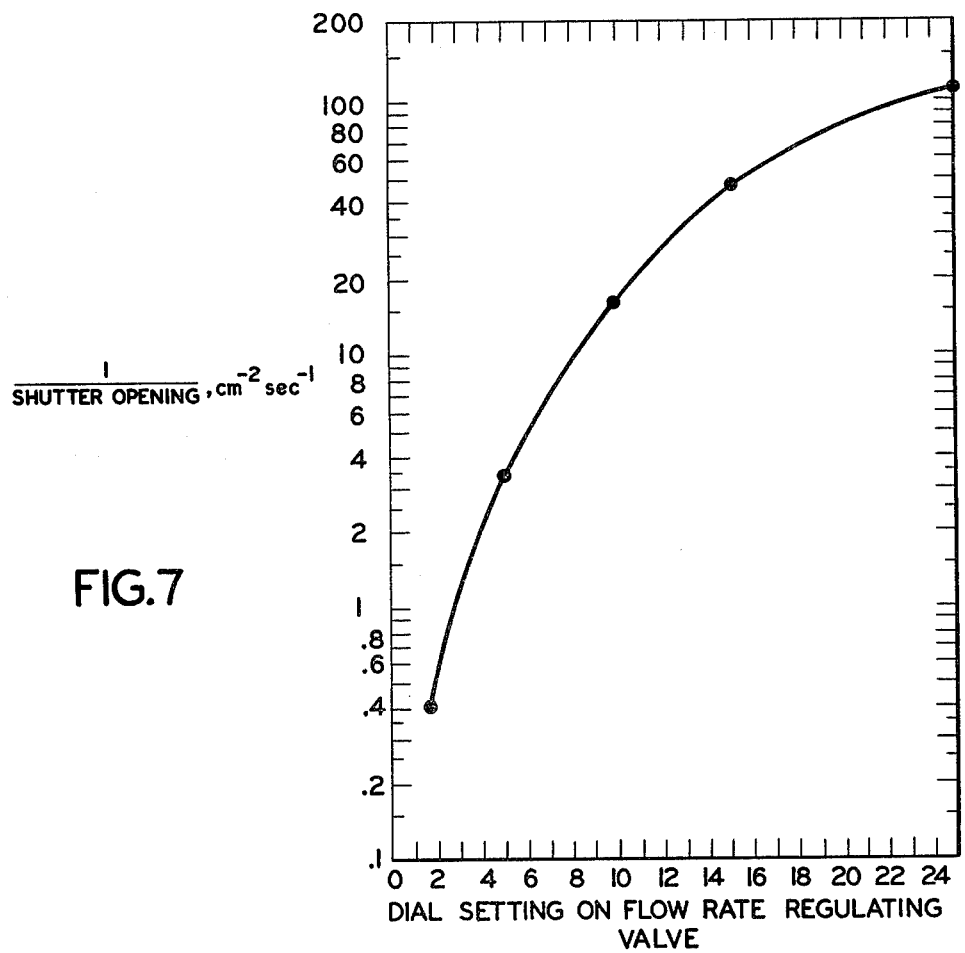
FIG.7
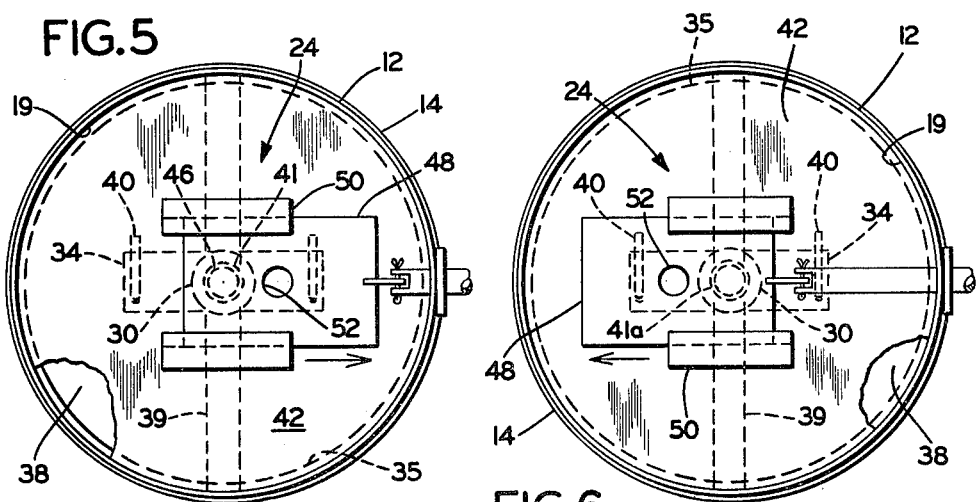
FIG.5
FIG.6

PORTABLE AIRBORNE DROPLET IMPACTOR SAMPLER AND METHOD

BACKGROUND ART

The present invention relates generally to methods of and apparatus for measuring characteristics of airborne droplets such as size and concentration distributions, and more particularly, toward a stain type droplet sampling method and apparatus using a pneumatically operated shutter to control exposure time, wherein droplet size error caused by impact flattening is compensated and droplet deposition rate is measured as a function of stain count and shutter speed.

Knowledge of drop velocity and especially drop size concentration distribution is important in such fields as the scavenging of airborne particles by raindrops, the elimination of drop carry-over from cooling towers and dust suppression by water sprays. In a belt transfer station or other mining environment, for example, once drop size distribution, concentration and velocity are known, the spray nozzle for optimum dust suppression due to impact coverage can be selected based upon geometry, desired degree of coverage and local line pressure.

Although drop velocity for droplets of several hundred microns in diameter can be estimated in many applications, most nozzle manufacturers do not provide adequate information on droplet size and concentration to enable proper selection. Laboratory methods for measuring these parameters are available, but are complex and expensive. One form of portable droplet sampler is formed of a magnesium oxide coated, glass slide that is exposed for a predetermined time duration to airborne droplets and receives a permanent impression or stain from each droplet impacting the surface of the slide. The stains are counted and diameters measured for correlation with drop size and concentration distribution.

Because there is a "flattening effect" of a droplet in air deviating from its ideal spherical shape upon impact with a target, the stain imparted to the magnesium oxide layer will typically be larger than the actual droplet size. The effect of impact velocity of incident droplets on a target has not been previously fully understood. Drops, always heterogeneous in size, impact a solid surface at different fractions of terminal velocities, especially when the droplets fall from a limited height. Accurate measurement of droplet size by the stain technique requires a method of correcting the stain diameters to the true diameter of the incident droplet.

Engelmann, for example (see Engelmann, R. J., *The Hartford Raindrop Sampler and Selected Spectra*, A.E.C. Resource and Development Report, H.W. -73119, 1962), has developed a calibration curve that relates stain and drop diameters to each other. The incident drop must impact the target surface at a known velocity (usually the terminal velocity). In practice, however, physical constraints often limit the sampler location to be less than that required for the droplet to acquire terminal velocity. For example, a 0.60 millimeter diameter droplet requires a falling height of 200 centimeters to attain a fully developed terminal velocity whereas a 20 millimeter diameter droplet attains only 78% of its terminal velocity at the same height and requires 1,400 centimeters to reach its terminal velocity. Neglect of the non-terminal velocity effect for the 2.0 millimeter diameter droplet would lead to an apparent drop diameter that is 25% larger than the true diameter.

Equations have been developed that relate stain diameter to actual droplet diameter at droplet velocities that are less than terminal velocity, as set forth in Cheng, *Environmental Science Technology*, 11, 192 (February, 1977). In order to apply these equations to determine actual droplet size of droplets at impact velocities less than terminal velocity, it is necessary to provide a magnesium oxide layered planchet to obtain accurate stains caused by droplet impact. We have found, however, that prior art stain type droplet sampler devices are incapable of obtaining highly accurate droplet size and distribution readings.

In May, "The Measurement of Airborne Droplets by the Magnesium Oxide Method", *Journal of Scientific Instruments*, Volume 27, 1950, there is described a stain type droplet target using a thick magnesium oxide coating which retains stains when impacted by airborne droplets. The magnesium coating is deposited on a glass substrate at a thickness of 40–500 microns and at least 90% coverage of the target surface. We have found that the thick coating of magnesium oxide tends to acquire rough stain edges which cause inaccuracy in measurement of stain diameters. Also, due to limited dispersion of the magnesium oxide granules, the thick layer fails to distinguish whether a given stain is a result of one or more incident droplets.

Another deficiency of the prior art stain type droplet samplers has been that exposure time to ambient droplets is not accurately controlled and the exposure time is not easily varied. In Grantham, *A Journal of Applied Meteorology*, Volume 4, page 1293, 1975, for example, a thick magnesium oxide layer stain device is exposed to airborne droplets through a rubberband operated, rotary shutter. In practice, the shutter provides only a limited range of exposures and thus is unable to measure high or low droplet concentrations. There still exists a need, therefore, for a stain type, airborne droplet sampler that enables higher accuracy droplet size and distribution measurements than heretofore provided in the prior art.

Accordingly, one object of the present invention is to provide a new and improved airborne droplet impact sampler that provides highly accurate droplet stains when impacted by airborne droplets.

Another object of the invention is to provide a new and improved air droplet sampler that is capable of exposing an impact stain target to airborne droplets for a precisely controlled period of time.

Another object of the invention is to provide a new and improved airborne droplet sampler that is capable of exposing a droplet stain target to airborne droplets for a variable sampling period.

Another object of the invention is to provide a new and improved airborne droplet sampler stain type target that has improved stain resolution and is capable of distinguishing multiple impact stains.

Another object of the invention is to provide a new and improved airborne droplet sampler that is simple, light in weight and convenient to operate at remote locations.

DISCLOSURE OF INVENTION

A drop impactor sampler, in accordance with the invention, comprises a target in the form of a graphite planchet coated with a very thin (less than about 5 microns) layer of magnesium oxide and positioned below a shutter mechanism within an open ended, cylindrical sampling head. The shutter comprises a stationary plate having an orifice aligned with the target and a movable plate guided to slide along the surface of the stationary plate. The movable plate has an orifice that is positioned to sweep along a common diameter with the stationary orifice to provide the shutter action.

The movable orifice plate is controlled by a single action pneumatic cylinder that is powered by an air source mounted on an elongated handle carrying the sampler head. Air pressure is applied to operate the piston through a calibrated regulator so that the shutter velocity is very precisely controlled.

The target is positioned on a microscope slide that is retained on the base of a restraining member by a pair of spring biased clips. The restraining member is in the form of an inverted cup that is retained by friction against the inner wall of the cylindrical sampler head. The cup is applied to and removed from the sampler through its open lower end by a gripper bar that transverses the cup.

At the upper end of the sampler head, a removable cover is provided with a raised central portion defining an inlet aperture to limit the incoming droplets to the vicinity of the target. Beneath the movable orifice plate, there is a ring member having an upper rim in the form of a knife edge to function as a splash guard to assure that only complete droplets enter the target area.

The sampler is operated by first positioning the sampler head with its shutter closed a predetermined distance below a source of droplets to be sampled. After choosing an appropriate shutter speed by operating the pressure regulator, the shutter is operated by opening a valve which causes the piston of the single acting air cylinder to sweep the movable orifice plate across the stationary orifice plate and thereby expose the target to incoming droplets for a precisely controlled period of time. The target is then removed from the sampler head for analysis of stain count and size. Droplet size and concentration are determined from the stain analysis using tables.

Still other objects and advantages of the present invention will become readily apparent to those skilled in this art from the following detailed description, wherein we have shown and described only the preferred embodiment of the invention, simply by way of illustration of the best mode contemplated by us of carrying out our invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF DRAWINGS

FIG. 1 is a top view of the airborne droplet impact sampler with its cover removed to expose internal structure;

FIG. 2 is a side view of the sampler shown in FIG. 1;

FIG. 3 is a cross sectional side view of the sampler head showing the movable orifice plate in a retracted position prior to sampling;

FIG. 4 is a cross sectional side view corresponding to FIG. 3 with the orifice plate in an extended position following a sampling operation;

FIG. 5 is a top view of the sampler head showing the movable orifice plate in the retracted position;

FIG. 6 corresponds to FIG. 5 with the movable orifice plate in an extended position;

FIG. 7 is a graph showing shutter speed as a function of dial setting of the flow rate regulating valve shown in FIGS. 1 and 2;

DETAILED DESCRIPTION OF A PREFERRED EMBODIMENT

Figure 9:
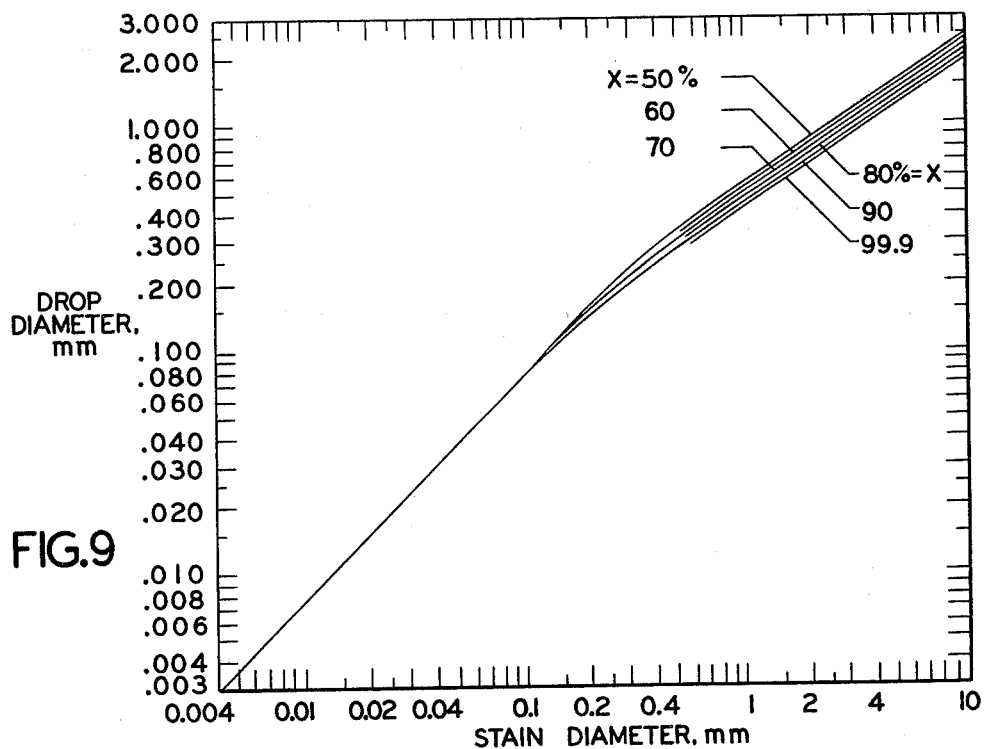
FIG. 9 is a plot of drop diameter versus stain diameter as a function of percentage terminal velocity obtained from the graph of FIG. 8.

Referring to FIGS. 1 and 2, an airborne droplet impact sampler, designated generally by the numeral 10, comprises a sampler head 12 supported opposite handle 18 of an extension rod 13 by straps 14 and 16. The sampler head 12 is in the form of a cylinder having open upper and lower ends 19 and 20 and containing a droplet target 22 (see FIGS. 3 and 4) exposed to candidate droplets through a shutter mechanism 24 and the central aperture 26 of a removable cover plate 28. The upper end 19 of sampler head 12 is partially enclosed by a cover 28 shown in FIGS. 3 and 4 (the cover is removed in FIGS. 1 and 2 for clarity). The cover 28, which is seated within the head 12 by annulus 27, has a raised center portion 29 defining the aperture 26. Aperture 26 is positioned on the axis of target 22 to limit incoming droplets to the region of the target. Preferably, the cover 28 is formed of a transparent plastic material to enable inspection of the interior of head 12 by the human operator.

Droplet target 22 is a graphite substrate 30 coated at its upper surface with a very thin layer 32 of magnesium oxide. The thickness of the magnesium oxide layer 32 is on the order of no larger than five microns and in practice uniformly covers only approximately 10% of the target surface. This is considerably thinner than prior art droplet targets wherein the thickness of the magnesium oxide layer is typically one to two orders of magnitude larger and covers about 90% of the target surface. We have found that the substantially thinner layer of magnesium oxide provides a more accurate stain pattern than is possible with a thick layer. The stain edges are more precisely defined and dispersion of magnesium oxide granules tends to be much more sensitive to droplet impact. We have found, in fact, that it is possible to distinguish between single and multiple impact stains using the very thin magnesium oxide layer and graphite planchet combination since the color of the oxide coated target surface, which is initially gray, will lighten in response to single impacts, and lighten further in response to multiple impacts. In the prior art targets, on the other hand, single as well as multiple impacts on the thickly magnesium oxide layered glass substrate completely expose the glass surface making distinction impossible.

The target 22 is mounted on a glass microscope slide 34 which is in turn centrally positioned on the upper surface 36 of a restraining member 38. Member 38 comprises an inverted cup (see FIGS. 3 and 4) having a flat, circular base 36 defining the supporting surface for the slide 34. Member 38 is inserted into sampler head 12 through lower end 20 and is retained in place, as shown in FIGS. 3 and 4, by friction between the cylindrical wall of the member and inner wall surface of the sampler head 12. The glass slide 34 is retained on the surface 36 of restraining member 38 by a pair of conventional microscope slide spring clips 40 (see FIGS. 5 and 6). The rotational orientation of the slide 34 and target 22 is variable within sampler head 12 by first manually adjusting the rotational position of the member using rod 39 (FIG. 1) extending diametrically across the walls of restraining member 38. The member 38 is then manually urged upwardly into the sampler head 12 to create a friction fit.

Shutter 24, positioned within sampler head 12 above the target 22, comprises a stationary plate 42 mounted on an annular shoulder 35 formed on the inner wall surface of sampler head 12 and a movable plate 48. The stationary plate 42 has a centrally located orifice 46 just above the target 22. The movable plate 48 is positioned above stationary plate 42 and is guided for movement in a plane parallel to the stationary plate by a pair of guides 50 (see FIGS. 5 and 6) on opposite sides of the movable plate. A second orifice 52 formed in movable plate 48 has a diameter that is slightly smaller than that of orifice 26 in the stationary plate 42. The two orifices 46 and 52 formed respectively in plates 42 and 48 together constitute the shutter 24 which exposes target 22 to droplets entering impact sampler 12 through the aperture 26 formed in cover 28. A ring member 41 mounted on the stationary plate 42 around orifice 46 has a rim 41*a* in the form of a knife edge extending upwardly just below movable orifice plate 48. The ring member 41 functions as a splash guard for droplets entering the shutter 24 and to guide whole droplets through lower orifice 46 into contact with target 22.

With reference to FIGS. 1–6, one end of movable plate 48 is attached to an extension tube 51 that is controlled by a single acting air cylinder 54 (see FIGS. 1 and 2) to cause the movable plate to transverse the stationary plate 42. The movable plate 48 is positioned above the stationary plate 42 within guides 50 such that, when indexed by extender 54 between a first position (FIGS. 3 and 5) and a second position (FIGS. 4 and 6), the moving orifice 52 sweeps across the stationary orifice 46 along a common diametric axis. Thus, when the movable plate 48 is located in the first position, orifices 46 and 52 are non-overlapping, and the target 22 is blocked to droplets entering the sampler head 12 through cover aperture 26. Similarly, when the movable plate 48 is located in the second position, the two orifices 46 and 52 are non-overlapping. As the movable plate 48 indexes between the first and second positions, however, the moving orifice 52 will sweep above the stationary orifice 46 to cause increasing exposure of the target 22 to sample droplets until there is maximum exposure with the two orifices aligned along a common center. As the orifice 52 continues to index toward the second position, the exposure area will decrease until the two orifices again are non-overlapping. The velocity of the moving plate 48 is controlled by the amount of air pressure applied from air storage tank 56 to single acting air cylinder 54 through flow regulator 58, as described in detail below. The exposure area of the target 22 to sample droplets thus varies sinusoidally as a function of time and is controlled by regulator 58.

Referring to FIGS. 1 and 2, the outlet of tank 56 is supplied to the regulator 58 through a three-way valve 60 controlled by valve operator 62 enabling the input to regulator 58 to be alternatively connected to air tank 56 or to a pressure release port 74. The magnitude of air pressure applied to the three-way valve 60 is controlled by pressure regulator 75 and monitored by a pressure gauge 64. The air storage tank 56 is recharged as required by an external source (not shown) through recharge valve 66 positioned between gauge 64 and the tank 56. A needle valve 68 controls air pressure generated at the outlet of tank 56.

The common outlet 77 of three-way valve 60 is coupled to the inlet of flow regulating valve 58 through a flexible hose 73. Regulator 58 is calibrated to pass a controlled amount of air pressure to cylinder 54 as a function of the rotational position of the body 58*a* of the regulator 58. The flow regulating valve 58, which is of conventional construction, is calibrated by dial markings (not shown) on the body portion 58*a* which enables direct calibration of shutter speed prior to each sampling cycle. Shutter speed versus dial setting of regulator 58 is shown graphically in FIG. 7, as discussed in detail below.

In practice, a target 22 is located on glass slide 34 on the surface of restraining member 38 which is initially outside the sampler head 12. The restraining member 38, now carrying the target 22, is located within sampler head 12 through open lower end 20 and is retained in place by friction. Cover 28 is applied to upper end 19 of sampler head 12, and the head is manually positioned using handle 18 into a sample region. With three-way valve 60 closed, needle valve 68 at the outlet of storage tank 56 is opened and pressure regulator 75 is rotated until a predetermined pressure monitored by gauge 64 is applied to port 70 of three-way valve 60. The pressure applied to valve 60 through pressure regulator 75 must be sufficient to enable the flow regulator 58 to receive enough air pressure to operate the air cylinder 54 throughout the adjustment range of the regulator 58. In practice, we have found that an air pressure of 40 pounds, as read from gauge 64, is sufficient for most droplet sampling applications.

With three-way valve 60 still closed, flow regulating valve 58 is adjusted to provide a predetermined shutter speed based upon experience and by the graph of FIG. 7 to provide a droplet distribution that is neither too small nor too large to generate meaningful data. Three-way valve 60 is now indexed to its second position to interconnect the output of pressure regulator 75 and the inlet of flow regulating valve 58 through flexible hose 73. Air pressure from tank 56 is thus applied to single acting air cylinder 54 to force movable orifice plate 48 to the left (FIG. 6) to expose target 22 to candidate droplets for a time period precisely determined by the dial setting of flow regulating valve 58.

Following a sampling cycle, the three-way valve 60 is operated to interconnect flow regulating valve 58 and pressure release outlet 74 on three-way valve 60 which exhausts air from cylinder 54 and regulator valve 58 into the atmosphere. The movable plate 48 is now manually retracted into the first position shown in FIG. 3 for another sampling cycle. The restraining member 38 is finally removed from impact head 12 through lower end 20 and stains on target 22 are analyzed to determine data including droplet count, size and concentration distribution.

When a droplet impacts the surface of the target 22, the drop flattens and leaves an imprint or stain. Microscopic examination of the target surface provides the droplet size and concentration distribution data.

With respect to water droplets impacting the surface of target 22, the droplet diameter and stain diameter D and S are related by:

$$D = \left( \frac{(1 - \cos\theta)^2 (S + \cos\theta)^{\frac{1}{3}}}{4\sin^3\theta} \right) S \quad (1)$$

and $$D = \left( \frac{9}{4} \frac{\sigma}{\rho_\omega C^4 V^2} \right)^{1/5} S^{4/5} \quad (2)$$

where
- $\theta$ is the mean contact angle of the droplet,
- $\sigma$ is the surface tension of water against air,
- $\rho_\omega$ is the density of water,
- V is impact velocity and
- C is the ratio of the experimental to theoretical stain diameter that is determined empirically. Details are given in Cheng, L., *Environmental Science Technology*, 11, 192 (February, 1977), incorporated herein by reference.

Equation (1) is applicable for droplets having diameters less than 0.12 millimeter with negligible impact velocity, and is based upon a spherical quiescent model. Equation (2) is applicable for droplet sizes larger than 0.3 millimeter and impact velocities greater than 150 centimeters per second, and is based upon a dynamic spreading model wherein the incident droplet spreads into a flat disk. Details of this analysis are described in Cheng, L., *I&EC Proc. Des. and Dev.*, 16, 192 (April, 1977), incorporated herein by reference. The value of C in equation (2) depends upon the nature of the liquid, the nature of the target, and the impact velocity; it is determined experimentally (see Cheng, L. articles, supra). Even assuming that C is unity, however, equation (2) predicts droplet size to within 16% for water droplets in most practical situations (0.2–1.4 millimeters diameter, 100–2,500 centimeters per second velocity). For drop diameters between 0.12 and 0.3 millimeter, and velocities equal to or less than the terminal values, equations (1) and (2) must be interpolated.

The value of the drop velocity V can be estimated for most practical situations, but can be conveniently related to the fraction x of the terminal drop velocity $V_t$, where $x = V/v_t$. The equation of motion of the drop falling under the force of gravity is $$(dV/dt) + x^2 g - g = 0 \quad (3)$$

where
- t is the time, and
- g is gravitational acceleration.

Since $V = dh/dt$, where h is the vertical distance, equation (3) becomes $$dh = \frac{V_t^2 \, x \, dx}{(1 - x^2) g} \quad (4)$$

Integration of equation (4) for zero initial height and initial vertical velocity gives $$h = -\frac{V_t}{2g} \ln(1 - x^2) \quad (5)$$

Figure 8:
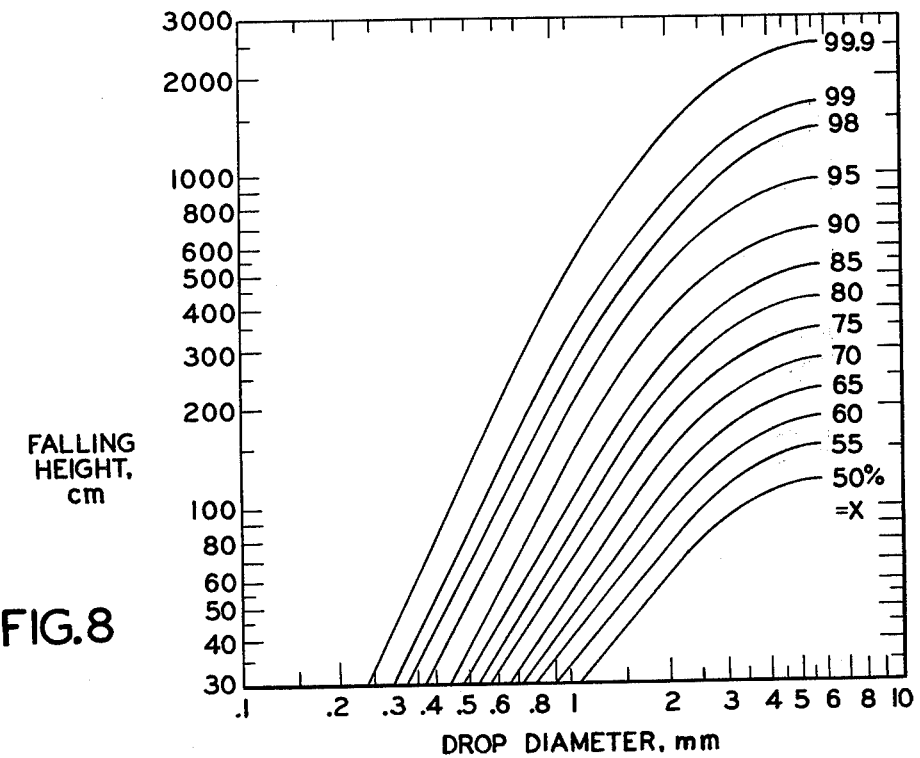
FIG. 8 is a graph showing a plot of falling height versus droplet diameter to determine percentage of terminal velocity.

The above relationships are illustrated graphically in FIGS. 8 and 9 which were generated by a computer based upon equation (5) and equations (1) and (2), respectively. FIG. 8 is a plot of percentage terminal velocity of droplets as a function of falling height and droplet diameter. In FIG. 9, droplet diameter is plotted as a function of stain diameter and percentage terminal velocity.

To determine actual droplet diameter from stain diameter, FIG. 8 is first used to obtain percentage terminal velocity of the droplet based upon the known falling height in centimeters on the ordinate and estimated drop diameter on the abscissa. The actual droplet diameter can be used to then calculate size distribution in a conventional manner.

The drop concentration distribution is obtained from the graph of FIG. 7 based upon stain count and the dial setting on flow rate regulating valve 58. Assuming, for example, that the dial setting is at numeral 8 and that 10 droplets on target 22 are counted, the reciprocal of shutter opening from the graph is determined to be 9.5 which is multiplied by the factor 10 (droplets) to obtain a rate of disposition of 95 droplets per square centimeter. Knowing the rate of deposition as well as impact velocity (equation (5) and FIG. 8), concentration distribution can be calculated in a conventional manner.

In this disclosure, there is shown and described only the preferred embodiment of the invention, but, as aforementioned, it is to be understood that the invention is capable of use in various other combinations and environments and is capable of changes or modifications within the scope of the inventive concept as expressed herein.

We claim:

1. A drop impactor sampler, comprising:
   a target having an upper surface which, when struck by a droplet, retains an impression corresponding to droplet size;
   a stationary plate positioned adjacent said target and containing a first orifice through which said target is exposed to droplets to be sampled;
   a movable plate parallel to said stationary plate and containing a second orifice;
   means for moving said movable plate between first and second positions at a predetermined velocity; and
   means for guiding said movable plate to maintain said first and second orifices along a common diametric axis between said first and second positions, said first and second orifices being non-overlapping with said movable plate located in said first position or said second position;
   said movable plate and said stationary plate forming a shutter for selectively exposing said target to the external droplets for a period of time corresponding to said predetermined movable plate velocity.

2. The sampler of claim 1, wherein said target comprises a graphite planchet coated with a thin layer of magnesium oxide.

3. The sampler of claim 2, wherein said magnesium oxide layer has a thickness less than about 5 microns.

4. The sampler of claim 1, wherein said sampler further comprises a cylindrical sampler head having open upper and lower ends, said shutter and said target being located within said cylindrical head on a central axis thereof.

5. The sampler of claim 4, wherein said target is supported on a restraining member frictionally engaged with an inner wall surface of said cylinder.

6. The sampler of claim 5, wherein said restraining member comprises an inverted cup member, a base of said cup member supporting said target.

7. The sampler of claim 6, including a gripping rod extending across said cup member to enable manual insertion and removal of said cup member relative to said sampler head.

8. The sampler of claim 5, wherein said target is mounted on a glass slide carried by said restraining member.

9. The sampler of claim 1, wherein said moving means includes a pneumatic cylinder and means coupling together a piston of said cylinder and said movable plate.

10. The sampler of claim 9, including an extension rod extending outwardly from said shutter and said target, said pneumatic cylinder mounted on said extension rod, and means for controlling pneumatic pressure applied to said piston.

11. The sampler of claim 4, including a cover plate mounted to an upper end of said cylinder, said cover plate having a central aperture for receiving droplets to be impacted on said target.

12. The sampler of claim 8, including clip means for retaining said glass slide on said restraining member.

13. The sampler of claim 11, further including an air supply tank mounted on said extension rod for supplying pneumatic pressure to said piston.

14. The sampler of claim 13, wherein said pressure controlling means includes manually adjustable pressure flow regulating valve means for controlling air pressure applied to said pneumatic cylinder.

15. A method of measuring spatial concentration of droplets using a target of a type that retains an impression of each droplet impinging on its surface, and a shutter comprising relatively movable, parallel orifice plates for selectively exposing said target to droplets to be sampled, comprising the steps of positioning said target with the shutter closed in a region containing the droplets to be sampled; opening and then closing said shutter at a predetermined velocity to expose the target to the droplets for a predetermined time duration; counting the droplet impressions on the target, and correlating the count with shutter speed to obtain droplet concentration.

16. A method of measuring the diameters of water droplets in air released from a falling height h using a stain target selectively exposed to the droplets through a shutter comprising relatively movable, parallel orifice plates, wherein the impact velocity of the droplet is less than its terminal drop velocity, comprising the steps of exposing the target to said droplets through said shutter for a predetermined period of time by moving one of said plates relative to the other at a predetermined velocity to cause temporary overlapping of a pair of orifices formed respectively in the two plates, measuring the diameters of the stains imparted to said target by impacting droplets, determining percentages of terminal velocity of said droplets at impact and compensating said stain diameters as a function of the percentage terminal velocities and measured stain diameters to determine actual droplet diameter prior to impact.

* * * * *